United States Patent [19]

Flynn

[11] 3,993,095

[45] Nov. 23, 1976

[54] POSITIVE PRESSURE RESUSCITATOR

[76] Inventor: Stephen Donald Flynn, 7410 Manion Road, Mississauga, Ontario, Canada

[22] Filed: Dec. 27, 1973

[21] Appl. No.: 428,823

[52] U.S. Cl. .......................... 137/596.1; 128/145.8; 128/210
[51] Int. Cl.² ............................................ A62B 7/02
[58] Field of Search ................ 128/145.8, 196, 203, 128/205, 210, 145.5; 137/596, 596.1, 596.12, 596.2

[56] References Cited
UNITED STATES PATENTS

| 196,185 | 10/1877 | Boekel | 137/596.2 X |
|---|---|---|---|
| 2,870,763 | 1/1959 | Stanton | 128/145.8 |
| 3,566,866 | 3/1971 | Adams | 128/145.8 |
| 3,605,803 | 9/1971 | Walker | 137/596.1 |
| 3,805,780 | 4/1974 | Cramer et al. | 128/145.8 X |
| 3,874,378 | 4/1975 | Isaacson et al. | 128/145.8 |

FOREIGN PATENTS OR APPLICATIONS

| 1,159,743 | 7/1958 | France | 128/145.8 |

*Primary Examiner*—Alan Cohan
*Assistant Examiner*—Gerald A. Michalsky

[57] ABSTRACT

Apparatus for the administration of gases such as oxygen, anaesthetic gases, or the like, incorporating a chamber adapted to communicate with a face mask, gas delivery means for delivering gas into said chamber, valve means for intermittently discontinuing delivery of gas thereto, vent means for intermittently venting said chamber to atmosphere for exhalation, and, pressure relief valve means communicating with said chamber for venting the same to atmosphere in the event of an overpressure occurring therein.

1 Claim, 1 Drawing Figure

POSITIVE PRESSURE RESUSCITATOR

The present invention relates to apparatus for the administration of gases such as oxygen, anaesthetic gases and the like and is particularly designed to provide a resuscitator appliance which may be used first as a resuscitator and subsequently as an inhalator

BACKGROUND OF THE INVENTION

Respiration equipment may be divided into two main classes. The first class, namely resuscitators, are generally speaking designed for reviving a patient who has either ceased breathing, or who is breathing only with great difficulty. The other type of equipment, namely inhalators, supply gases or gas mixtures such as anaesthetics, or oxygen enriched air for speeding up the revival of a person who either has previously been revived with a resuscitator, or who is experiencing some respiration difficult, and requires assistance.

In the great majority of cases, it is highly desirable to have the two functions namely the resuscitator function and the inhalator function provided by the same piece of respiration equipment, with complete and instantaneous control over both functions without the need for leaving the patient to attend to a complex system of valves and gauges. In the past, dual-purpose apparatus of this kind has been available but has been of such a complex and cumbersome nature that either the operator would have to turn away from the patient to attend to various dials and gauges, or he would require an assistant. The desired coordination of the assistant handling the controls, with the operator who is actually in charge of the patient was of course quite difficult to achieve in many circumstances.

In addition, it is desirable to provide such a piece of equipment which can be operated in a simple foolproof manner by relatively unskilled personnel. It is of course be borne in mind that in many cases equipment of this kind is used in an emergency by the first person who is available to assist a casualty. Such a person will only in very rare cases be a highly trained medical assistant. In the great majority of cases such a person may be for example a lifeguard or swimming pool attendant, or a person on duty at an electrical generating station for example, or may be a relatively untrained fireman. In addition, the environment where such treatment is given is rarely if ever conducive to the careful and methodical application of professional medical skills. On the contrary, such an environment may be for example, several hundred feet under ground in a mine shaft, or at a breakdown in a generating or transformer station, or at the location of a fire. Such equipment must therefore be adapted for use by such relatively untrained personnel, who may in addition, be under considerable emotional or nervous strain due to the circumstances and the surroundings.

A further factor which must be borne in mind is the fact that the atmosphere at the location may not be conducive to respiration at all. For example, at a fire, or in a mine shaft, the air will usually be heavily contaminated and scarcely fit to breath. It is therefore highly desirable that such contamination shall be completely excluded from the respiration equipment.

As stated, equipment has been available in the past of a relatively complex nature which would provide the positive pressure resuscitation function, applying 100 percent oxygen under positive pressure to the casualty. However, it was difficult and cumbersome to convert such equipment to the inhalation function to permit free breathing with air enriched with oxygen after resuscitation had been successfully carried out. In addition, the control of such positive pressure apparatus required careful training and practice for satisfactory results which were not injurious to the casualty, for example, as a result of the application of an overpressure of oxygen to the lungs.

It is therefore desirable to provide a resuscitator apparatus which is simple to operate, and requires little or no training, and is designed to prevent accidental injury to the casualty, and which may readily be converted to an inhalator function by the operator without distracting his attention from the casualty.

BRIEF SUMMARY OF THE INVENTION

With these objectives in mind, the invention seeks to provide a resuscitator apparatus incorporating a passageway adapted to communicate with a face mask, oxygen delivery means for delivering oxygen into said passageway, valve means for intermittently discontinuing delivery of oxygen thereto, vent means for intermittently venting said passageway to atmosphere for exhalation, and, pressure relief valve means communicating with said passageway for venting the same to atmosphere in the event of an overpressure occurring therein.

More particularly, the invention seeks to provide a resuscitator apparatus having the foregoing advantages in which the operation of the vent means is coupled to the operation of said oxygen valve means, whereby upon closure of said oxygen valve means, said vent means is simultaneously opened, and whereby upon opening of said oxygen valve means or delivery of oxygen into said passageway, said vent means is simultaneously closed, thereby ensuring a positive pressure within said passageway for delivery of said oxygen to the casualty.

More particularly, it is an objective of the invention to provide a device of the type described incorporating a pressure relief valve which may be preset accurately for preventing injury to the casualty due to misuse of the equipment.

More particularly, it is an objective of the invention to provide a device of the type described having the, foregoing advantages incorporating a vent opening for exhalation by the casualty, which opening is normally open to establish free air flow between the interior and exterior of said passageway, and which is closed only by the action of opening the oxygen valve to admit oxygen therein.

It is a further and related objective of the invention to provide a device of the type described incorporating bypass conduit means for permitting oxygen to flow directly into said passageway without passing through said oxygen valve, and valve means for controlling said oxygen bypass flow.

The foregoing and other advantages of the invention will become apparent from the following description of a preferred embodiment of the invention which is given here by way of example only with reference to the following drawings.

DESCRIPTION OF A SPECIFIC EMBODIMENT

Figure 1:
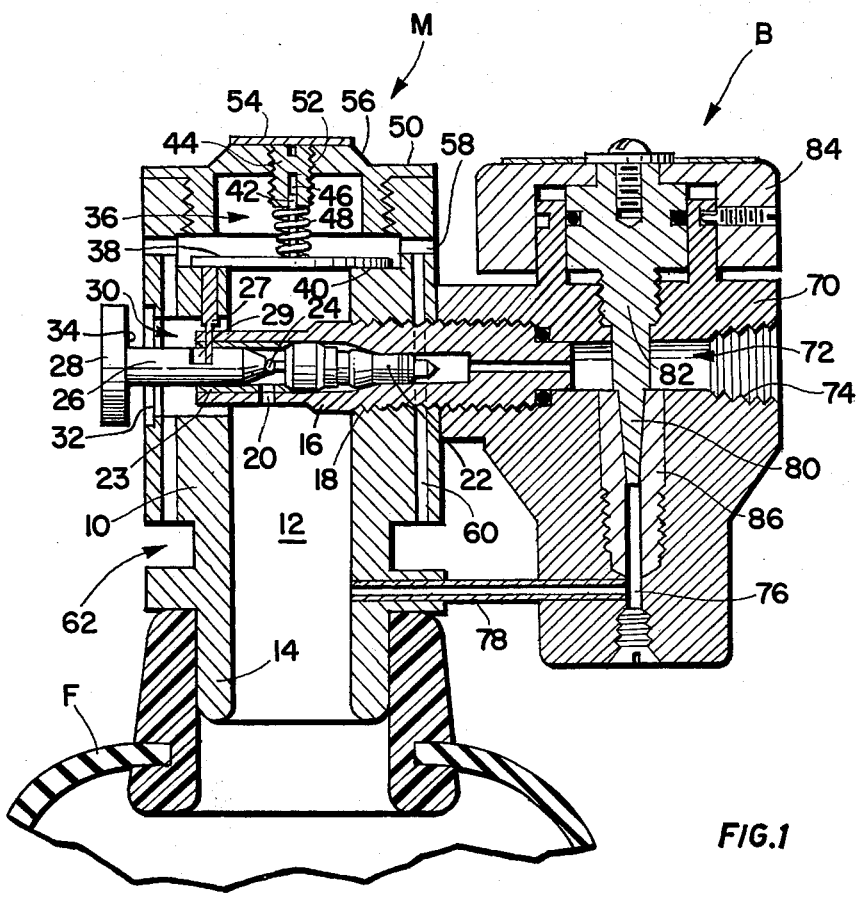
FIG. 1 is a sectional side elevational view of a resuscitator according to the invention.

As shown in the illustration, the resuscitator apparatus according to the invention will be seen to comprise a main body portion M and a bypass control B.

Referring first of all to the main body portion M it will be seen to comprise a tubular barrel 10 defining a hollow cylindrical chamber 12 and having a lower tubular extension 14. The lower tubular extension 14 will be of any suitable shape, and may have a slight exterior taper, if desired, so as to be fitted into one of a variety of different face masks F. It will of course be appreciated that different types of face masks may be used for different casualties, such face masks being omitted from the drawing for the sake of clarity and being in any event well known in the art.

Within the chamber 12, an oxygen delivery pipe 16 is threadedly fastened in the threaded opening 18. The oxygen delivery pipe 16 is provided with an outlet orifice 20 for discharging oxygen into the interior of the chamber 12. The pipe 16 extends outwardly from the main body 10, and is threadedly connected to the bypass valve B described below.

Within pipe 16, there is a spring loaded valve unit 22 secured by sleeve 23 and operated by means of a valve operating pin 24 extending therefrom. The valve 22 may be of any well known design such as is used in automobile and truck tires, and is not illustrated for the sake of clarity since the details are well known in the art. However, the valve 22 would normally be closed, and would be opened upon pressure being applied to the operating pin 24, the valve unit 22 including a spring (not shown) urging the valve closed as soon as the pin 24 is released.

In order to apply axial pressure to the operating pin 24, a pressure shaft 26 is slidably mounted in the open end of the pipe 16, and extends outwardly therefrom beyond the exterior of the body 10. A button 28 is fastened to the free end of the shaft 26 whereby the same may be manually pressed home to depress the operating pin 24 and open the valve 22.

A retaining pin 27 engages a slot 29 in shaft 26 to retain the same in the pipe 16.

In order to provide an exhalation port communicating between the chamber 12 and the exterior of the body 10, a port or opening 30 is formed in this body 10 co-axially with the oxygen pipe 16. The exhalation port 30 is of a greater diameter than the pipe 16 whereby to define a free space therearound around which air may flow in or out sufficiently freely to permit respiration by a patient.

In order the close the exhalation port during positive pressure resuscitation, a closure seat 32 is formed around the port 30, and a sealing surface 34 is formed on the underside of the button 28, which is designed to contact the seat 32 when the button 28 is depressed, and thereby close off and seal the exhalation port 30.

When button 28 is released it will be observed that it has sufficient clearance from the seat 32 to permit free flow of air into and out of port 30 to permit respiration by a patient as described.

In order to provide a pressure relief valve, a valve chamber 36 is provided at the top end of the body 10 formed essentially by an oversize counterbore co-axial with the cylindrical chamber 12. Within the valve chamber 36 a disc-like valve plate 38 is provided, fitting snugly against the valve seating surface 40. A supporting stem 42 extends axially upwardly from the center of the disc 38, and is supporting by the adjustment screw 44, formed with a suitable cylindrical recess 46 extending axially upwardly therein, and of a suitable size to permit the supporting stem 42 of the valve disc 38 to slide inwardly and outwardly.

A spring 48 is fitted around the stem 42 and extends between the lower end of the screw 44 and the upper surface of the disc 38, and normally urges the disc 38 in to its closed or seated position.

A top closure plate 50 threadedly engages and closes the top of the valve chamber 36, and is provided with a central threaded hole 52 for threadedly receiving the screw 44. Thus by adjusting the screw 44 inwardly or outwardly, the pressure exerted by the spring 48 on the valve disc 38 can be precisely regulated. Preferably, such regulation will be carried out in the factory, and the screw 44 will then be set so that it cannot lose its adjusted position.

In order to provide a finish, and to prevent tampering with the screw 44 any suitable cover means such as the adhesive metallic label 54 may be provided extending over the central portion of the cover 50 and concealing the screw 44. If desired, the cover 50 can be provided with a thickened portion 56 to provide a somewhat greater length for the threaded hole 52 thereby permitting a wider range of adjustment for the screw 44.

In order to permit escape of oxygen, or exhaled oxygen and air, in some cases, from within the valve chamber 46, a number of radial vent drillings 58 are formed at angularly spaced points around the main body 10 communicating with the interior of valve chamber 36, and a plurality of longitudinal vent drillings 60 are formed through the main body 10 at spaced points therearound, parallel with the central axis of the main body 10, and communicating with the annular recess 62. In this way, an overpressure causing the valve disc 38 to lift, may be relieved either through the vent openings 58 or through the vent openings 60 and 62, the vent opening 60 communicating with the radial openings 58 so that in the event that for example all of the radial openings 58 are covered by the hands of the operator, the pressure can still nevertheless be vented through the drillings 60 and the annular opening 62.

The bypass control B will be seen to comprise a main body portion 70, formed with a transverse cylindrical chamber 72. The one end of the chamber 72 the main body 70 is threaded to receive the delivery pipe 16, and establishes communication between the chamber 72 and the interior of the pipe 16. At the other end of the chamber 72, pipe threads 74 are formed for communication with any suitable oxygen supply system, consisting of a cylinder, with or without reducing valves and pressure gauges, all of which are well known in the art. In the majority of cases a flexible pressure hose (not shown) will be connected to the pipe threads 74 thereby permitting freedom of movement of the entire resuscitator unit, such hose being omitted for the sake of clarity.

In order to provide a continuous regulated bypass flow of oxygen, bypassing the valve 22, the bypass conduit 76 is provided communicating with the interior of the chamber 72, and a right angle bypass pipe 78 communicates between the lower end of the conduit 76, and enters the chamber 12 below the oxygen delivery pipe 16 as shown.

In order to regulate or entirely cut off flow of oxygen into the bypass conduit 76 and pipe 78, control is established by means of the tapered valve member 80 mounted on the threaded valve screw 82, which is threadedly received in a suitable threaded recess (not shown) formed in the main body 70. A knurled knob 84 is fastened to the top end of the valve screw 82 for rotating the same.

The tapered valve member 80 fits within a valve seat 86 fastened with in bypass conduit 76.

In operation, assuming the casualty requires positive resuscitation, oxygen will be supplied by any suitable source (as described above) directly into the chamber 72 of the bypass control B. At this point, the valve 80 will be seated firmly in the valve seat 86 thereby shutting off the bypass 76 and 80. Oxygen will thus be communicated directly to the valve 22. It cannot pass the valve 22 at this point since it is closed.

The attendant will then place the face mask F over the nose and mouth of the casualty, or in the case of a child for example over its entire face, depending upon the type of mask in use. The attendant will then depress the button 28 until the sealing face 34 contacts the seat 32. At this point, the valve pin 24 is fully depressed into the valve 22 and the valve 22 then passes oxygen through the interior of the pipe 16 and it can then pass out of the pipe 16 in through the port 20. At the moment when the valve 22 is first opened gas flows rapidly through opening 20. Such gas flow will initially tend to evacuate that part of the chamber 12 lying above the valve 22 and cause a slight momentary negative pressure. This will in turn draw the disc 38 more securely against the seat 40 thereby adding to the pressure of the spring 48. The flow of gas then establishes a positive pressure of oxygen within the chamber 12 which is therefore communicated directly to the face mask F, and hence to the casualty's lungs. Oxygen cannot escape from the chamber 12 through the port 30 since this is sealed and closed by the sealing surface 34 of the button 28 as described above.

Assuming that the casualty has no obstruction in the windpipe, then the oxygen will dilate the lungs. As soon as the attendant sees the chest of the casualty rise he will then release the button 28 and apply a gentle pressure to the chest to force the casualty to exhale. The releasing of the button 28 shuts off the valve 22 so that there is no further pressure of oxygen within the chamber 12. At the same time, it opens the port 30 thereby establishing free flow of oxygen from the chamber 12 to atmosphere. The pressure on the chest of the casualty will thus cause any oxygen within the lungs to flow outwardly to atmosphere. The attendant will then again press the button 28 and release the pressure on the casualty's chest, and continue until the casualty commences natural breathing.

Assuming that the attendant decides to continue supplying oxygen to the casualty when he has started breathing, then all the attendant has to do is to simply turn the knob 84 so as to permit a metered flow of oxygen through the bypass 76 and 78 directly into the chamber 12. The attendant then simply holds the face mask in position, but does not operate the button 28. Thus bypass flow of oxygen into the chamber 12 will be supplied within the face mask, and will be drawn into the casualty's lungs each time he breathes. Each time he exhales, the exhaled oxygen will flow outwardly through the port 30. In order to economize in oxygen, the flow rate of oxygen can be carefully controlled by positioning the knob 84, which may in fact carry a suitable marking (not shown) on its top surface indicating the approximate flow rate at any position. The casualty will then be able to breathe in, drawing in a mixture of atmospheric air which can flow inwardly through the port 30, and additional oxygen flowing through the bypass. The precise balance or proportioning between air and oxygen will of course be up to the attendant. If he feels for example that the atmospheric air available is unsuitable or undesirable he can simply increase the oxygen flow rate through the bypass so that the casualty will be breathing 100% oxygen, and no air will flow in through the port 30 due to the excess of oxygen being supplied to the chamber 12 through the bypass. On the other hand, if the atmospheric air is uncontaminated and suitable, then the oxygen flow rate could be reduced in order to conserve supplies.

In the event that the casualty has some obstruction in the windpipe, which has not become apparent to the attendant from his initial examination, then when the attendant presses the button 28 to obtain positive pressure resuscitation oxygen cannot flow from the face mask directly into the lungs. Thus the pressure within the chamber 12 will build up. It is of course essential to prevent any overpressure beyond a certain point since it might have the effect of either forcing the obstruction further down the windpipe for example. In order to prevent such a build up of overpressure the pressure relief valve disc 38 and spring 48 are so set that the disc 38 will lift off the seat 40 if the pressure reaches 40 mm. of mercury above atmospheric. Thus any overpressure in the chamber 12 will simply be released through the pressure relief valve mechanism, and will escape through the ports 58 or 60 to atmosphere.

Similarly, if the equipment is being used by an inexperienced attendant he may have a tendency to continue holding the button 28 shut long after the casualty's lungs have filled and the chest has risen. If there were no provision for a pressure relief system such a method of operation could be dangerous to the patient and result in over-dilation of the lungs. Again, this dangerous situation is avoided by presetting the blow-off pressure of the disc 38 by means of the adjustment screw 44 so that the blow-off occurs precisely at 40 mm. of mercury.

Thus even with a completely inexperienced operator positive pressure resuscitation can be safely applied by means of the apparatus without danger to the patient. In addition, the pressure relief valve being located within the actual control device, will give an audible warning of the over-pressure as soon as it develops. This is because the operation of the valve is of course momentary that is to say it will lift off against its spring 48, release the overpressure and snap down again and do so continuously fluttering up and downwardly, until the operator releases the button 28, and removes the obstruction from the windpipe. Similarly, this fluttering will occur if the button 28 is held closed after the lungs have been fully dilated. The fluttering of the valve disc 38 provides an audible clicking sound which gives an immediate warning to the attendant that an overpressure exists so that he can immediately act accordingly.

Preferably the flow rate of oxygen through the bypass B, when this is in use, will be adjustable between about 0 – 15 liters per minute.

The flow rate available under positive pressure resuscitation, through the main body M will preferably be in the order of 70 liters per minute, although of course in this case, flow is intermittent, and oxygen will not in practice be used at this rate.

Reference has been made throughout to oxygen, as the gas used. It will however be understood that gases other than oxygen could be administered by use of the foregoing apparatus such as various types of anaesthetics or oxygen mixed with any other gas or gases, where the same provide advantageous treatment.

The term oxygen used herein, is therefore to be taken as non-limiting, and it is intended that the term shall embrace any such gas or gases as may be administered.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. Apparatus for the administration of gases, such as for resuscitation, inhalation or the like, said apparatus comprising;
    chamber means adapted to communicate with a face mask or the like for administration of gas;
    gas delivery means for delivering said gas into said chamber;
    valve means for intermittently discontinuing delivery of gas thereto;
    vent opening means communicating with said chamber, and having closure means therefore, intermittently operable to open and close said vent opening means whereby to permit intermittent exhalation through said chamber and vent opening means;
    pressure relief means communicating with said chamber for venting the same to atmosphere in the event of an overpressure developing therein, and,
    bypass connection means communicating with said gas delivery means, and bypass conduit means communicating between said bypass connection means and said chamber means, and manually operable bypass valve means for controlling flow of gas through said bypass conduit means, whereby to permit bypass flow of gas into said chamber means without restriction by said valve means.

* * * * *